(12) United States Patent
Alarcon et al.

(10) Patent No.: US 11,978,540 B2
(45) Date of Patent: May 7, 2024

(54) SYSTEM FOR COLLECTING AND TRANSMITTING SMOKER DATA

(71) Applicant: Fontem Holdings 4 B.V., Amsterdam (NL)

(72) Inventors: Ramon Alarcon, Los Gatos, CA (US); Dennis Christopher Howard, Summerfield, NC (US)

(73) Assignee: Fontem Ventures B.V., Amsterdam (NL)

( * ) Notice: Subject to any disclaimer, the term of this patent is extended or adjusted under 35 U.S.C. 154(b) by 785 days.

(21) Appl. No.: 16/745,893

(22) Filed: Jan. 17, 2020

(65) Prior Publication Data

US 2020/0152301 A1 May 14, 2020

Related U.S. Application Data

(62) Division of application No. 14/899,098, filed as application No. PCT/US2014/043742 on Jun. 23, 2014, now abandoned.

(60) Provisional application No. 61/837,860, filed on Jun. 21, 2013.

(51) Int. Cl.
| | |
|---|---|
| *A24F 40/10* | (2020.01) |
| *A24F 40/00* | (2020.01) |
| *A24F 40/40* | (2020.01) |
| *A24F 40/50* | (2020.01) |
| *A24F 40/65* | (2020.01) |
| *G01D 9/00* | (2006.01) |
| *G16H 10/60* | (2018.01) |
| *G16H 40/67* | (2018.01) |

(52) U.S. Cl.
CPC .............. *G16H 10/60* (2018.01); *A24F 40/40* (2020.01); *A24F 40/50* (2020.01); *A24F 40/65* (2020.01); *G01D 9/00* (2013.01); *G16H 40/67* (2018.01); *A24F 40/00* (2020.01); *A24F 40/10* (2020.01)

(58) Field of Classification Search
CPC .......... A24F 40/00; A24F 40/10; A24F 40/40; A24F 40/50; A24F 40/65; G01D 9/00; G16H 10/60; G16H 40/67
See application file for complete search history.

(56) References Cited

U.S. PATENT DOCUMENTS

| | | | |
|---|---|---|---|
| 8,550,069 B2 | 10/2013 | Alelov | |
| D700,994 S | 3/2014 | Alarcon et al. | |
| 8,851,081 B2 | 10/2014 | Fernando et al. | |
| 10,131,532 B2 * | 11/2018 | Murison | F04B 19/006 |
| 10,973,258 B2 * | 4/2021 | Alarcon | A61M 15/06 |
| 2004/0031498 A1 * | 2/2004 | Brue | A24F 15/00 |
| | | | 131/270 |
| 2009/0283103 A1 | 11/2009 | Nielsen et al. | |
| 2010/0177508 A1 * | 7/2010 | Maglica | F21V 31/03 |
| | | | 362/183 |

(Continued)

FOREIGN PATENT DOCUMENTS

| | | | | |
|---|---|---|---|---|
| CN | 202172847 | * | 3/2012 | ............. A24F 47/00 |
| CN | 202172847 U | | 3/2012 | |
| WO | 2013040275 A1 | | 3/2013 | |

*Primary Examiner* — Abdullah A Riyami
*Assistant Examiner* — Thang H Nguyen
(74) *Attorney, Agent, or Firm* — Dykema Gossett PLLC

(57) ABSTRACT

A system and device for collecting and delivering smoker statistics to an external storage device that accurately describe a smoker's smoking habits.

16 Claims, 14 Drawing Sheets

(56) References Cited

U.S. PATENT DOCUMENTS

| | | |
|---|---|---|
| 2011/0277764 A1* | 11/2011 | Terry ................... A61M 11/042 128/203.26 |
| 2012/0199146 A1* | 8/2012 | Marangos ............... A24F 40/50 131/328 |
| 2012/0295487 A1* | 11/2012 | Villarreal .............. G06F 1/1632 439/660 |
| 2013/0284192 A1 | 10/2013 | Peleg et al. |
| 2013/0340775 A1* | 12/2013 | Juster ................. H04L 12/1827 131/273 |
| 2014/0107815 A1 | 4/2014 | LaMothe |
| 2014/0174459 A1* | 6/2014 | Burstyn ................. A24F 40/60 131/273 |
| 2014/0246035 A1 | 9/2014 | Minskoff et al. |
| 2014/0278250 A1 | 9/2014 | Smith et al. |
| 2014/0278258 A1 | 9/2014 | Shafer |
| 2015/0020832 A1 | 1/2015 | Greim et al. |
| 2015/0224268 A1 | 8/2015 | Henry et al. |
| 2016/0278435 A1* | 9/2016 | Choukroun ............ A24F 40/50 |
| 2016/0371437 A1* | 12/2016 | Alarcon .................. G01D 9/00 |
| 2023/0204168 A1* | 6/2023 | Bertken .................. H04Q 9/00 315/149 |

\* cited by examiner

SYSTEM FOR COLLECTING AND TRANSMITTING SMOKER DATA

CROSS REFERENCE TO RELATED APPLICATION

This application is a divisional application of U.S. application Ser. No. 14/899,098, filed 16 Dec. 2015 (the '098 application), which is a national stage application based upon international application no. PCT/US2014/043742, filed 23 Jun. 2014 (the '742 application), which claims the benefit of U.S. provisional application No. 61/837,860, filed 21 Jun. 2013 (the '860 application). The '098 application, the '742 application, and the '860 application are all hereby incorporated by reference in their entirety as though fully set forth herein.

BACKGROUND

1. Field of the Present Disclosure

The present disclosure is directed to a smart electronic cigarette that may collect and transmit smoker statistics to an external storage device that may accurately describe a smoker's smoking habits.

2. Related Art

Electronic cigarettes, also known as e-cigarettes (eCigs) and personal vaporizers, are electronic inhalers that vaporize or atomize a liquid solution into an aerosol mist that may then be delivered to a user. A typical eCig has a mouthpiece, a battery, a liquid storage area, an atomizer, and a liquid solution. Smokers who try to reduce their smoking or who would like to monitor their smoking habits for any of a variety of reasons, including clinical studies, have to personally monitor and record their smoking habits.

SUMMARY

According to one non-limiting example of the disclosure, a system, a method, a device and a computer program are provided for collecting and delivering smoker statistics to an external storage device that accurately describe a smoker's smoking habits.

In one embodiment, a system for collecting and transmitting smoker data comprises a data logging device configured to be removably coupled to a cigarette and to collect smoker data from the cigarette; and a docking station comprising a docking port configured to mate with the data logging device, the docking station configured to enable transmission of the smoker data from the data logging device to a user interface.

In another embodiment, a method for collecting and transmitting smoker data comprises associating a smoker identification with an electronic cigarette; collecting smoker data from the electronic cigarette; transmitting the smoker data to an external storage device; and providing the smoker data to a user, the smoker data being associated with the smoker identification.

Additional features, advantages, and embodiments of the disclosure may be set forth or apparent from consideration of the detailed description and drawings. Moreover, it is to be understood that the foregoing summary of the disclosure and the following detailed description and drawings are exemplary and intended to provide further explanation without limiting the scope of the disclosure as claimed.

BRIEF DESCRIPTION OF THE DRAWINGS

The accompanying drawings, which are included to provide a further understanding of the disclosure, are incorporated in and constitute a part of this specification, illustrate embodiments of the disclosure and together with the detailed description serve to explain the principles of the disclosure. No attempt is made to show structural details of the disclosure in more detail than may be necessary for a fundamental understanding of the disclosure and the various ways in which it may be practiced. In the drawings.

DETAILED DESCRIPTION

The disclosure and the various features and advantageous details thereof are explained more fully with reference to the non-limiting embodiments and examples that are described and/or illustrated in the accompanying drawings and detailed in the following.

Figure 1:
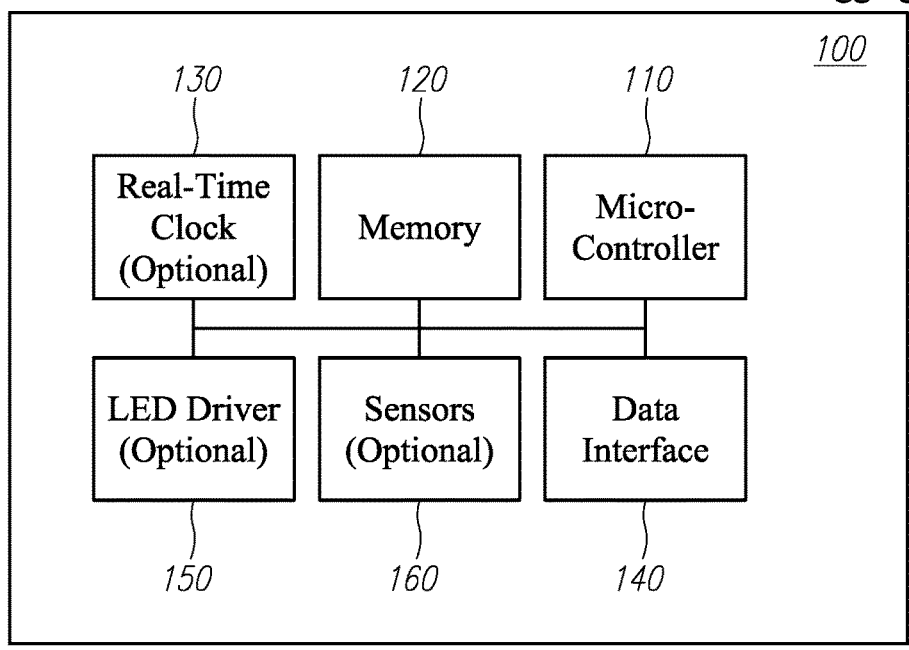
FIG. 1 shows an example of a data logging device constructed according to the principles of the disclosure.

FIG. 1 shows an example of a data logging device 100, according to an aspect of the disclosure. The data logging device 100 comprises a microcontroller 110, a memory 120, and a data interface 140. The microcontroller 110 comprises a computer. In one embodiment, the microcontroller 110 can control the data logging function run by the data logging device 100. In another embodiment, the microcontroller 110 can control the data logging function run by the data logging device 100 and can also govern other functions of the SCig. The memory 120 includes a computer-readable medium. The data interface 140 is configured to transmit and/or receive (transceive) logging data signals and control signals from/to the data logging device 100 via a communication link. The data interface 140 may include a power supply line that may be connected to an external power supply. The data interface 140 may be configured to interface with existing circuitry in a conventional eCig (e.g., eCig 10 shown in FIG. 3). In one embodiment the microcontroller 110 can track time, by either having a clock built into the microcontroller 110 or by having a timer that is integral to the microcontroller 110 and can track the amount of time that has passed since a certain point or since a signal or other mechanism was received. In a separate embodiment, the logging device 100 can further comprise a real-time clock 130 to track the amount of time between certain events or to report an internal reference time to a different component of the data logging device 100. The data logging device 100 can also optionally include a light emitting diode (LED) driver 150. The LED driver 150 can send signals to operate an LED (not shown) that can be used as an operational indicator or other visual signal for the end user. The data logging device 100 can optionally also include various sensors 160. The sensors 160 can comprise a resistance measuring circuit, a thermocouple, a thermistor, a photoreceptor, an infrared measuring device, a current sensor, a flow sensor, a pressure sensor, or other similar sensors. These sensors can allow the microcontroller 110 to set or vary the energy delivered to a heating element, the volume of liquid delivered to a heating element in the SCig, or otherwise determine and change various settings within the SCig. The settings can vary, for example, when a slower and lower volume puff is being taken by a user and when a quick and deep puff is being taken by a user.

The data logging device 100 may further include a global positioning satellite (GPS) receiver (not shown), a Bluetooth device, a wireless internet device, and/or a radio frequency identification (RFID) device.

Figure 6:
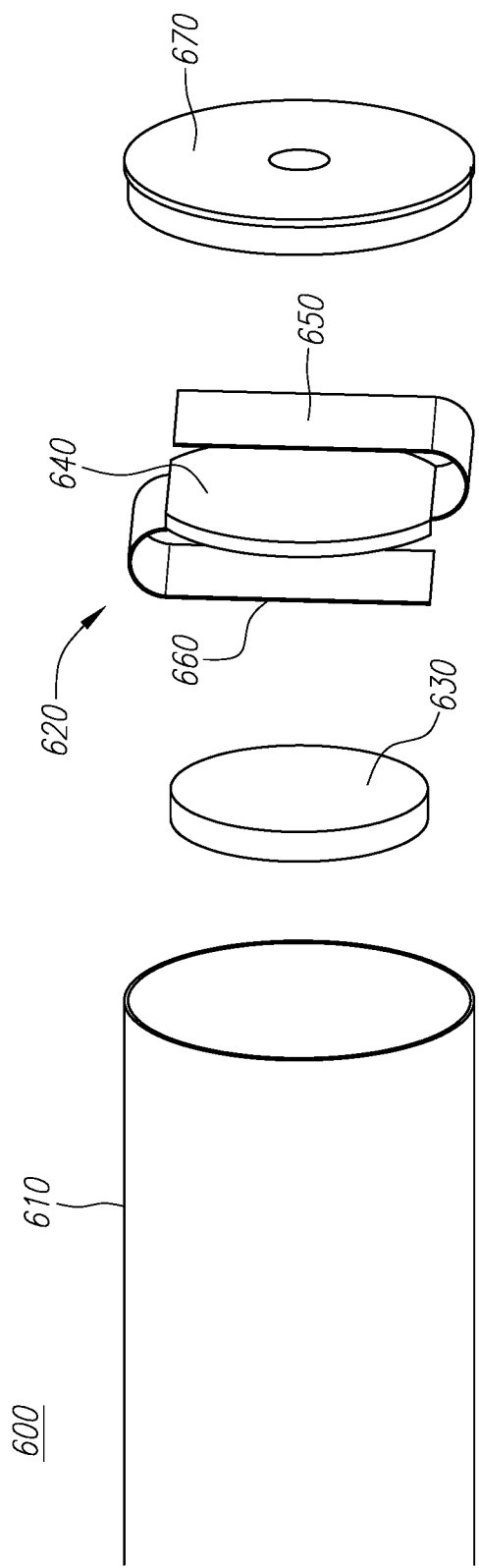
FIG. 6 shows an example of a mouthpiece that may be attached to a traditional tobacco-based cigarette, according to the principles of the disclosure.

A data logging device 100 as discussed in the present disclosure may be a dedicated circuit within an SCig or a retrofitting unit (as seen in FIG. 6), or may be incorporated into circuitry that governs the SCig or the retrofitting unit.

Figure 2:
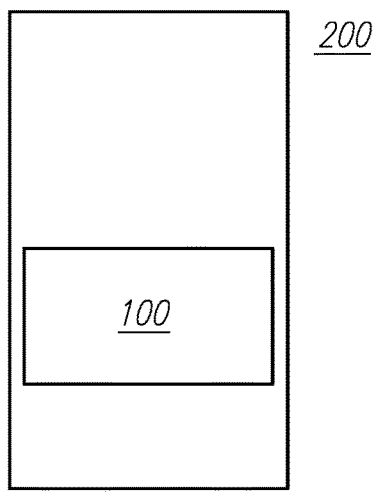
FIG. 2 schematically shows an example of a smart eCig (SCig) constructed according to the principles of the disclosure.

FIG. 2 shows an example of an SCig 200. In this embodiment, the SCig 200 includes the logging device 100 (shown in FIG. 1), a power supply (not shown), a mouthpiece (not shown), a liquid or gel solution (a juice) (not shown), and an atomizer (not shown). The SCig 200 may further comprise a liquid storage area (not shown) and/or a heating element (not shown). The data logging device 100 can be removably coupled to the SCig 200. Alternatively, the data logging device 100 can be irremovably coupled to a portion of SCig 200, such as the atomizer (or housing of the atomizer) or the power supply (or housing of the power supply).

Figure 3:
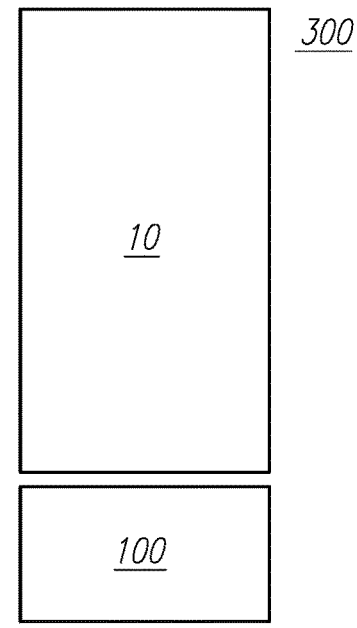
FIG. 3 schematically shows an example of a conventional eCig that is retrofitted with the logging device of FIG. 1 to make an SCig according to the principles of the disclosure.

FIG. 3 shows an example of a conventional eCig 10 that is retrofitted with the logging device 100 (shown in FIG. 1) to make an SCig 300, according to principles of the disclosure. The eCig 10 may include a conventional electronic cigarette such as, e.g., a blu™ Original, a blu™ Premium, a blu™ Premium 100, or the like.

Referring to FIGS. 1-3, the microcontroller 110 monitors and stores logging data in the memory 120. The logging data comprises SCig log data relating to the characteristics and conditions of the SCig 200/300, including its components (e.g., heating element, liquid storage area, atomizer, juice, battery, etc.) and user activity log data relating to the use of the SCig 200/300 by a user. On the basis of the logging data, the microcontroller 110 may control the amount and timing of delivery of the aerosol payload to the user, including, e.g., the nicotine payload, flavorant payload, as well as control one or more components in the SCig 200/300, including, e.g., the temperature of the heating element, the duration of operation of the SCig 200/300, the amount of juice aerosolized, the rate of aerosol generation, and the like.

The microcontroller 110 may include artificial intelligence (AI) such as, e.g., fuzzy logic, neural network, adaptive algorithms, or the like, so as to acquire historical user log data and customize operation of the SCig 200/300 to the user. The microcontroller 110 may process the logging data and run a predictive algorithm to predict user behavior to take anticipatory actions with regard to the SCig 200/300, such as, e.g., waking the SCig 200/300 from a sleep mode (or setting to sleep) at a particular time and/or date, activating (or deactivating) the heater element at a particular time/date, operating (or turning off) the heater element for a determined duration, and the like. The microcontroller 110 may also wake the SCig 200/300 from a sleep mode (or set to sleep) based on the logging data, including, e.g., a predetermined date, the manufacturing date, and the like.

SCig log data can comprise data such as, e.g., date of manufacture of the SCig (and/or a component in the SCig), expiration date of the SCig (and/or a component in the SCig), amount of time the SCig has been in use (e.g., hours of operation), power supply voltage, battery type, battery power remaining, number of times battery has been recharged, temperature of heater, heater type, nicotine level delivered, flavor in use, ingredient list, amount of cartomizer left, lot number, cartomizer type, cartomizer identification number, time/date of retrofitting the eCig 10 with the logging device, and the like.

The user activity log data comprises data such as, e.g., time of each use by the user (e.g., puff time), day of the week of each use by the user (e.g. puff day), date of each use by the user (e.g., puff date), duration of each use (e.g., puff duration), geographic location at each use (e.g., puff location), pressure during each use (e.g., puff draw strength or pressure), volume of each use (volume of puff), nicotine level delivered (payload) to user at each use (e.g., nicotine per puff), identification of ingredients in aerosol delivered to user at each use (e.g., ingredient identification), amount of each ingredient in aerosol delivered to user at each use (e.g., ingredient amount), user identification, user age, number of years user has been smoking, average number of cigarettes smoked per day by user, and the like.

Figure 4A:
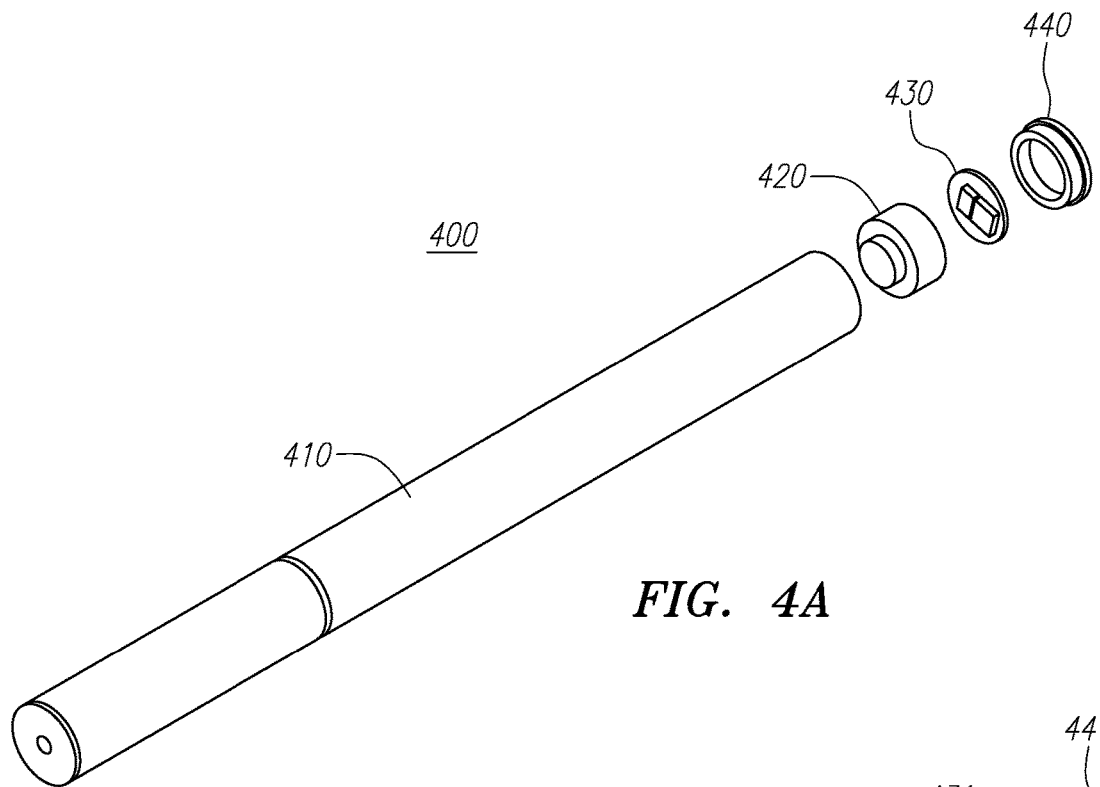
FIG. 4A shows an exploded, isometric view of an example of a conventional eCig that has been retrofitted according to the principles of the disclosure to form an SCig.

FIG. 4A shows an exploded view of an embodiment of an SCig 400 that is constructed according to the principles of the disclosure. The SCig 400 comprises a conventional eCig 410 and a removable/attachable data logging circuitry 430. The SCig 400 may comprise a data logging circuitry board support 420 and/or a cover (e.g., a lens) 440. The cover 440 may be an original part of the conventional eCig 410. The data logging circuitry 430 may include the logging device 100 (shown in FIG. 1).

The conventional eCig 410 may be retrofitted with the data logging circuitry 430 by removing the existing lens cover (e.g., cover 440), if any exists, inserting the data logging circuitry board support 420, inserting the data logging circuitry 430 and replacing (or placing) the cover 440. The data logging circuitry board support 420 may include contact points and/or communication links for conveying the logging data signals and control signals between the conventional eCig 410 and data logging circuitry 430. The control signals may include sensor signals received from one or more sensors provided in the conventional eCig 410, such as, e.g., a pressure sensor (not shown), a temperature sensor (not shown), a voltage sensor (not shown), a capacitive sensor (not shown), or the like. The data logging circuitry board support 420 may include a configuration that is configured to receive the data logging circuitry 430 and hold it snuggly suspended within the SCig 400 to minimize any forces that may be encountered, such as, e.g., dropping of the SCig 400.

In one embodiment the data logging circuitry board support 420 can already be included within the pre-retrofitted eCig 410. The data logging circuitry board support 420 can comprise a pre-existing circuitry (not shown). The pre-existing circuitry can be used by the eCig 410 to determine when a user is using the eCig 410 and/or to send visual signals to a user. In this embodiment the data logging circuitry board support 420 can be pre-existing circuitry, and the data logging circuitry 430 can be connected to the data logging circuitry board support 420. The data logging circuitry board support 420 can provide control signals to the data logging circuitry 430.

Figure 4B:
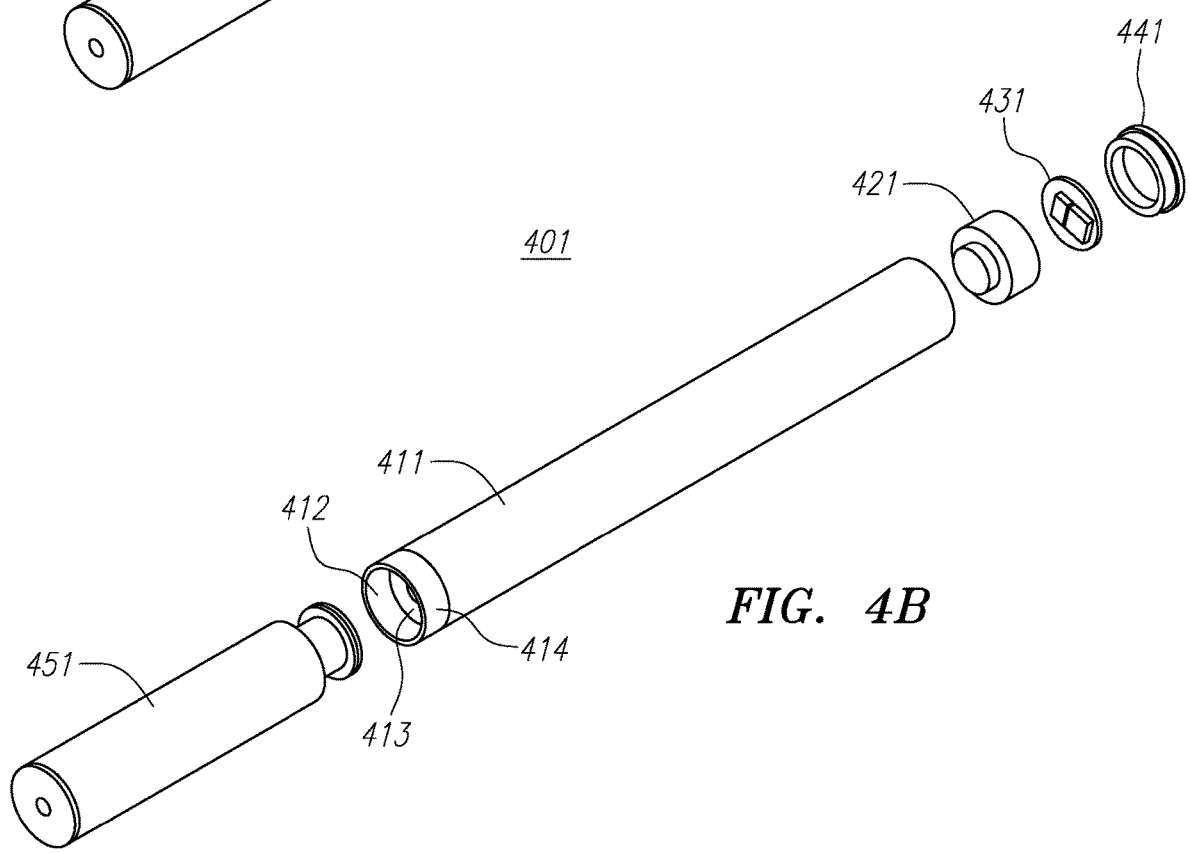
FIG. 4B shows an exploded, isometric view of an example of a rechargeable eCig that has been retrofitted according to the principles of the disclosure to form a rechargeable SCig.

FIG. 4B shows an exploded view of another embodiment of an SCig 401 that is constructed according to the principles of the disclosure. The SCig 401 comprises a conventional rechargeable eCig battery (not shown) that resides in tubular housing 411, a cartomizer 451 that also resides in a tubular housing, and a removable/attachable data logging circuitry 431. In this embodiment, the SCig 401 can further comprise a data logging circuitry board support 421, adapted to support the data logging circuitry 431, and a cover 441. The cover 441 can comprise a lens or device to cover one end of the SCig 401. The data logging circuitry 431 can comprise the logging device 100 (shown in FIG. 1).

In the depicted embodiment, the rechargeable eCig battery in housing 411 can be retrofitted with the data logging circuitry 431 by removing the existing cover 441, if present, coupling the data logging circuitry board support 421 and the data logging circuitry 431 to the rechargeable eCig battery, and connecting the cover 441 to the rechargeable eCig battery housing 411. In the current embodiment, the charging connection 412, which comprises first and second electrical contacts 413,414, respectively, that are in electrical contact with the positive and negative terminals (not shown) of the battery residing in the housing 411, can be configured for connection to the cartomizer 451, for connection to a charging station or device (see, for example, FIG. 13), and can also serve as a data connection to a pack, a fixture, a computer, or a different networked device. When the charging connection 412 is connected to a device that can send or receive data communications, the data logging circuitry 431 or other electronic circuit present on the SCig 401 can connect through the charging connection 412. The data logging circuitry board support 421 may include contact points and/or communication links for conveying the logging data signals and control signals between the conventional eCig 411 and data logging circuitry 431. The control signals may include sensor signals received from one or more sensors provided in the conventional eCig 411, such as, e.g., a pressure sensor (not shown), a temperature sensor (not shown), a voltage sensor (not shown), a capacitor sensor (not shown), or the like. The data logging circuitry board support 421 may include a configuration that is configured to receive the data logging circuitry 431 and hold it snuggly suspended within the SCig 401 to minimize any forces that may be encountered, such as, e.g., dropping of the SCig 401.

In one embodiment the data logging circuitry board support 421 can already be included within the housing 411. The data logging circuitry board support 421 can comprise a pre-existing circuitry (not shown). The pre-existing circuitry can be used by the rechargeable eCig battery to determine when a user is using the eCig and/or to send visual signals to a user. In this embodiment the data logging circuitry board support 421 can be pre-existing circuitry, and the data logging circuitry 431 can be connected to the data logging circuitry board support 421. The data logging circuitry board support 421 can provide control signals to the data logging circuitry 431 In another embodiment the data logging circuitry 431 can send and receive signals by modulating data on to the charge line and responding to data modulated onto the charge line by a pack, a fixture, a computer, or a different networked device.

Figure 5:
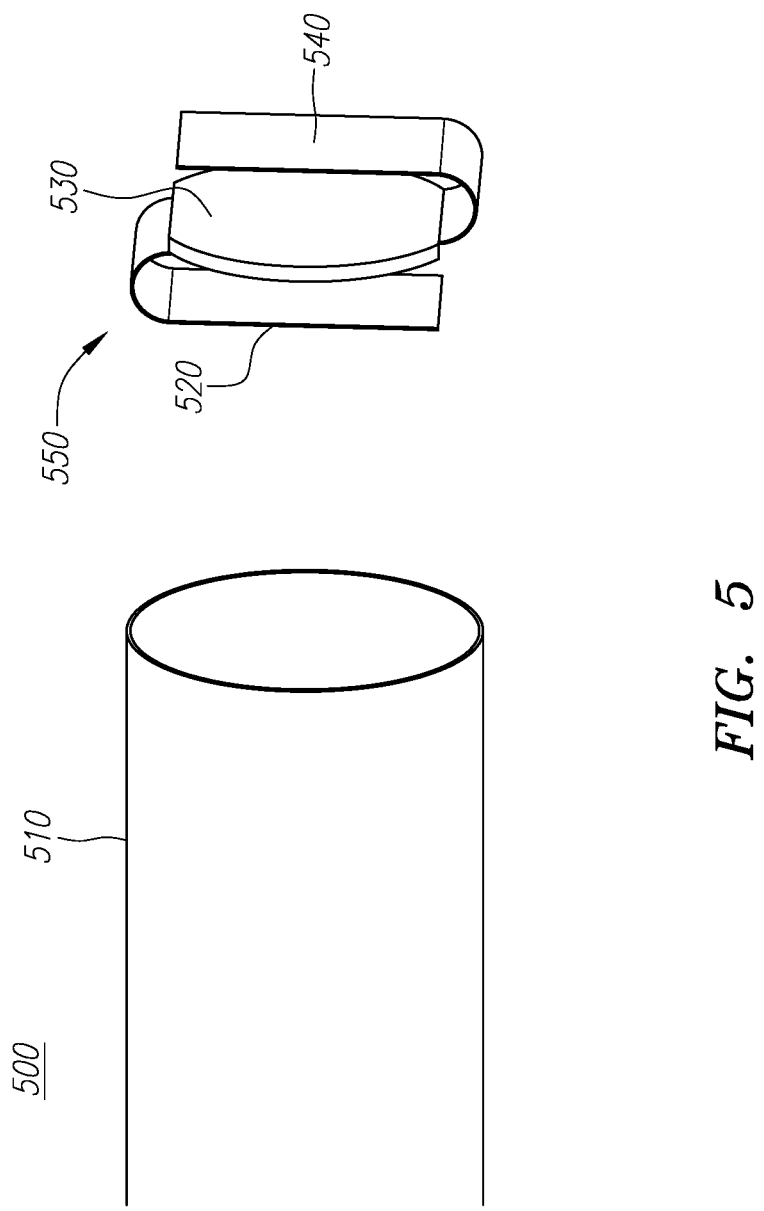
FIG. 5 shows another example of an SCig that is constructed according to the principles of the disclosure.

FIG. 5 shows an embodiment of an SCig 500 that is constructed according to the principles of the disclosure. The SCig 500 comprises a conventional eCig 510 and an attachable/insertable retrofitting unit 550. The retrofitting unit comprises a first contact portion 520 and a data logging circuitry 530. The first contact portion 520 may include communication links, including, e.g., a bus, a contact pin, a data line, electrical wire, ribbon cable, or the like. The data logging circuitry 530 may include the logging device 100 (shown in FIG. 1). The data logging circuitry 530 may include an LED. The data logging circuitry 530 can comprise a transducer (not shown), such as, e.g., an LED, an infra-red diode, an antenna, or the like. The data logging device 530 can be configured to broadcast data to an external device. The LED can be utilized by the SCig 500 to send visual indications to a user. The visual indications can include whether the SCig 500 is on, and whether the SCig 500 needs recharging, among other indications. The retrofitting unit may comprise a second contact portion 540. The second contact portion 540 may include communication links. In one embodiment, the second contact portion 540 may include a transducer (not shown), such as, e.g., an LED, an infra-red diode, an antenna, or the like. The second contact portion 540 can be configured to broadcast data to an external device. The first and/or second contact portions 520, 540 may be made of a clear plastic material that may allow a light beam emitted from the data logging circuitry 530 to travel through the first and/or second contact portions 520, 540; and the first and/or second contact portions 520, 540 may be configured to suspend the data logging circuitry 530 in the eCig 510 of the assembled SCig 500. The first contact portion 520 can comprise an interface that is separate from the interface comprising part of the second contact portion 540. In another embodiment, the first contact portion 520 and the second contact portion 540 can be integrated into a signal contact portion (not shown). In one embodiment, the retrofitting unit 550 can be removed from the SCig 500. The retrofitting unit 550 can be removed from the SCig 500 and the first contact portion 520 can be connected to a fixture or other device for downloading data thereto.

FIG. 6 shows an example of a mouthpiece 600 that may be attached to a traditional tobacco-based cigarette (not shown). The mouthpiece 600 comprises a housing 610, a retrofitting unit 620, a power source 630, and a cap 670. The housing 610 is configured to receive and securely hold a filter end of a traditional cigarette at one end of the housing 610. The housing 610 is further configured to receive and hold the retrofitting unit 620 and the power source 630 at its other end. The retrofitting unit 620 may include first and/or second contact portions 660, 650, which may be configured to suspend the data logging circuitry 640 in the housing 610 in the assembled mouthpiece 600. The retrofitting unit 620 can include a data logging circuitry 640, which can include the logging device 100 (shown in FIG. 1). The retrofitting unit 620 and/or the first and/or second contact portions 660, 650 can include one or more sensors (not shown) to measure airflow, time of day, puff frequency, puff duration, puff strength, puff volume, temperature of smoke, temperature of the cigarette filter, pressure, nicotine payload delivered to user, gas and particulate phase component delivery to user, and the like. The cap 670 encloses the retrofitting unit 620 within the housing 610.

Figure 7A:
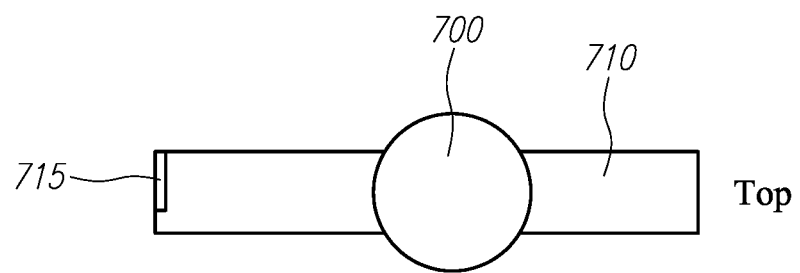
FIG. 7A shows a top view of an example of a retrofitting unit that is constructed according to the principles of the disclosure.

FIG. 7A shows a top view of an example of a retrofitting unit that is constructed according to the principles of the disclosure. The retrofitting unit comprises a logging device 700, a first contact portion with contacts 710 and a second contact portion with contacts 715. The logging device 700 may be substantially the same as the logging device 100, shown in FIG. 1.

Figure 7B:
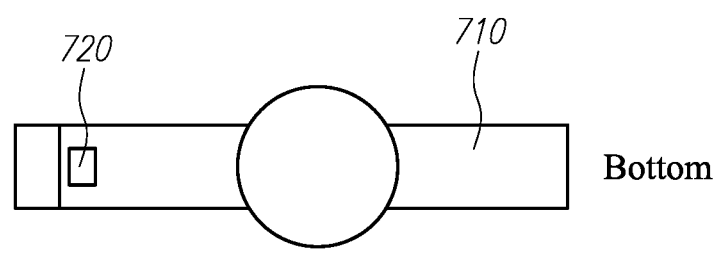
FIG. 7B shows a bottom view of the retrofitting unit of FIG. 7A.

FIG. 7B shows a bottom view of the retrofitting unit of FIG. 7A. As seen, the retrofitting unit may include an LED 720. In various embodiments the LED 720 can be placed on the logging the device, the first contact portion with contacts 710, and/or the second contact portion with contacts 715.

Figure 8:
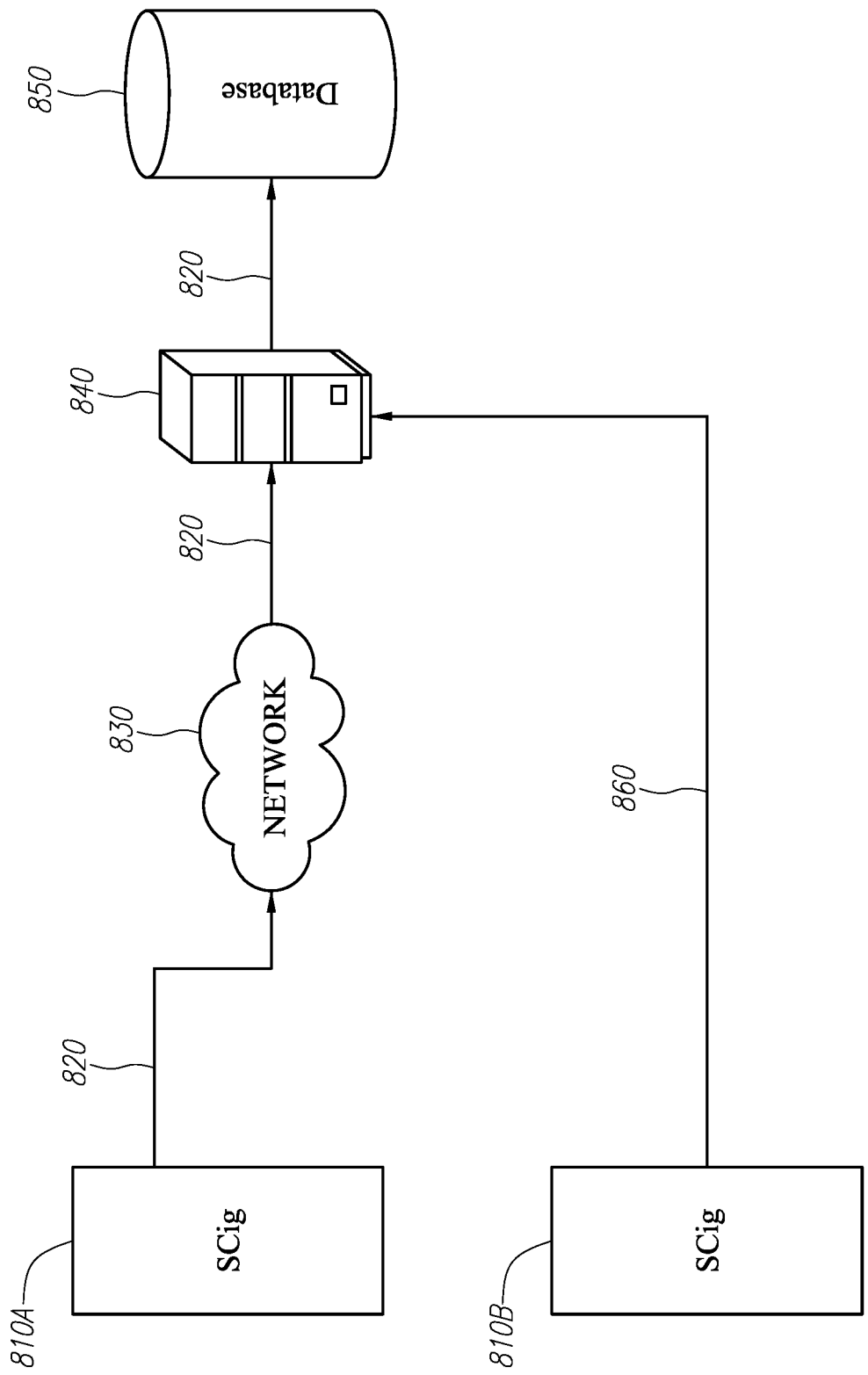
FIG. 8 shows an example of a system for monitoring, storing, and processing logging data, according to one aspect of the disclosure.

FIG. 8 shows an example of a system for monitoring, storing, and processing logging data, according to one aspect of the disclosure. The system of FIG. 8 may include one or more SCigs such as, e.g., SCigs 810A, 810B, a network 830, a computer 840, and/or one or more databases 850. The computer 840 may be, e.g., a workstation computer, a server, or a plurality of servers. The computer 840 and one or more databases 850 may be coupled to each other and/or the network 830 through one or more communication links 820. Alternatively, one or more database 850 may reside within the computer 840. SCigs such as SCig 810A may be coupled to the network 830 via communications link 820. Alternatively, SCigs such as SCig 810B may be coupled to computer 840 via a direct connection 860. The direct connection may be, e.g., a wired connection resulting from SCig 810B being coupled to a docking station such as docking stations 1004 (shown in FIG. 10A), an infrared connection, a Bluetooth connection, or the like. Alternatively, e.g., the logging device 100 may be detached from the SCig 810B and placed into a fixture/docking station similar to docking station 1040 (shown in FIG. 10B) that is configured to receive the SCig 810B or data logging device 100. SCigs 810A, 810B may include, e.g., an SCig 200, 401 that was manufactured to include a data logging device 100, an SCig 300, 400 created from a conventional eCig 10, 410, 510 that was retrofitted to include a data logging device, or a conventional tobacco cigarette coupled to a data logging device 100.

Figure 9:
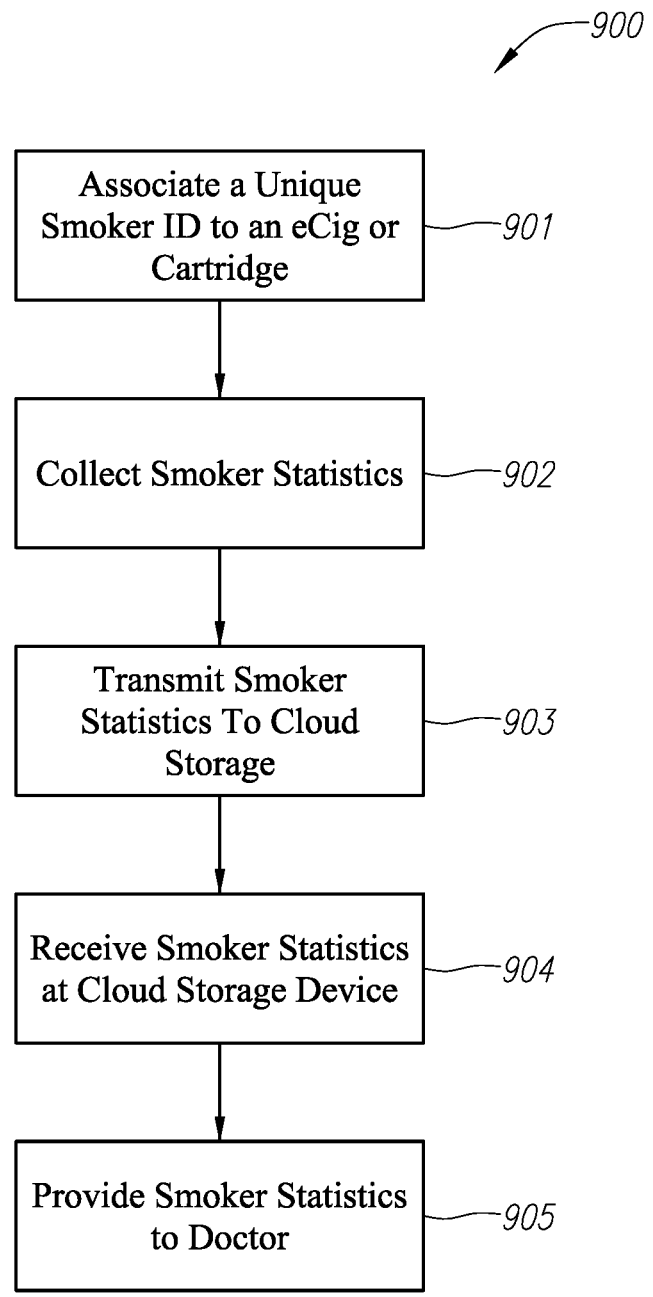
FIG. 9 shows an example of a method for collecting and wirelessly transmitting smoker statistics from the memory of an SCig to a cloud storage device, according to one aspect of the disclosure.

FIG. 9 shows an example of a method 900 for collecting and wirelessly transmitting smoker statistics from the memory unit 120 of an SCig to an external storage device such as, e.g., a cloud storage device, in accordance with one aspect of the disclosure. At step 901, a unique smoker identification (ID) may be generated. The unique smoker ID may include any data sufficient to associate a particular smoker with a particular SCig such as, e.g., an SCig serial number, an SCig barcode, a cartomizer serial number, a custom data string provided by the manufacturer of the SCig, a smoker's name, a smoker's social security number, a custom data string provided by the smoker, information from a cartomizer, or the like. The unique smoker ID may be generated, e.g., at the time a user purchases the SCig, or alternatively, e.g., at a point in time later than the time a user purchases the SCig via mail, telephone, or an online transaction via a network such as, e.g., the Internet.

Step 902 occurs after a smoker comes into possession of the SCig, becomes associated with a unique smoker ID, and begins using the SCig. While a smoker is using the SCig, microcontroller 110 interfaces with sensors in order to collect smoker statistics. After obtaining the smoker statistics, the microcontroller 110 may associate the unique smoker ID with the obtained smoker statistics in the form of, e.g., a data record. The data record may then be stored in the memory unit 120 permanently or temporarily until, e.g., a data transmission or data transfer is initiated.

At step 903 the data transmission module is used to transmit the data record to an external storage device such as, e.g., a cloud storage device. The cloud storage device may include, e.g., a server, or plurality of servers, associated with a database. The cloud storage device may receive the transmitted data record at step 904 and store the received data record in one or more databases 850 residing within the cloud.

In addition to storing the smoker statistics in the cloud, the cloud storage device may be associated with one or more servers 840 (shown in FIG. 8) that facilitate processing of smoker statistics. One or more of the servers 840 may, e.g., mine the smoker statistics in order to identify trends, characteristics, or other facts that may be implicit in the stored smoker statistics. For example, the smoker data may be processed in order to identify shared, or related, characteristics between one or more smokers. Based on the shared or related characteristics, servers 840 may inform each particular smoker about other members of the community that share similar or related characteristics, thereby prompting the smokers to, e.g., possibly meet up at social gatherings in the future or engage in virtual competitions to see who smoked the most or least. Such identified characteristics, and the subsequent notifications, may be utilized as a dating service or other type of social network.

Alternatively, or in addition, other processing of smoker statistics may include, e.g., processing of smoker statistics for advertisement related purposes. The processing of smoker statistics stored in the cloud may, e.g., result in the development of targeted advertising schemes. For example, the smoker statistics may be analyzed to determine that a smoker likes a particular flavor of cigarette solution, or other SCig product feature, and send the smoker notifications including advertisements for the flavored cigarette solution, or other SCig product feature. In addition, or alternatively, smoker statistics may also be analyzed to determine GPS data, or other location information, that indicates, e.g., the locations where a user tends to smoke. However, such examples should not be construed as limiting the scope of the processing that may take place in accordance with the principles of the disclosure. Any data mining, data analysis, or data massaging technique known in the art may be applied to the vast store of smoker statistics accumulated in, e.g., one or more databases 850, in order to yield lucrative networking and marketing data.

Similarly, the cloud storage device may be associated within one or more servers 840 (shown in FIG. 8) that facilitate monitoring of smoker statistics. Such monitoring may be set in place by, e.g., a doctor, in order to assist in the enforcement of a developed regimen. For example, a doctor may submit a plurality of one or more commands via graphical user interface to one or more servers 840 in order to define predetermined monitoring criteria for a particular smoker associated with a particular SCig. Such monitoring criteria may include, e.g., predetermined thresholds for SCig use by a particular smoker. The thresholds may define, e.g., a schedule that determines when a user can or cannot smoke (e.g., a user may be able to use the SCig on Mondays, Wednesdays, or Fridays but not Tuesday, Thursday, Saturday, or Sunday). Alternatively, e.g., the thresholds may define a total block of time that a user may smoke (e.g., user may be allotted 6 hours of smoke time per week). Alternatively, e.g., the thresholds may define a particular set amount of nicotine that is to be dispensed by the SCig. Alternatively, or in addition, e.g., thresholds may define geographical locations where a smoker is permitted to smoke and geographical locations where a smoker is not permitted to smoke. One or more servers 840 may then, e.g., transmit a plurality of one or more commands that activates the SCig for use within the thresholds defined by a particular schedule.

However, if a user attempts to use the SCig in a manner that exceeds any one or more of the thresholds associated with a predetermined schedule, one or more servers 840 may transmit one or more commands to disable the SCig by, e.g., powering off the SCig. In addition, e.g., a smoker may receive an alert when a smoker uses the SCig in a way that exceeds any one or more of the thresholds associated with a predetermined schedule. The alert may be provided, e.g., in addition to powering off the SCig or as an alternative to powering off the SCig. The alert may include, e.g., an email, SMS message, MMS message, or other form of message sent via a mobile phone, computer, or SCig pack. The alert may also include, e.g., prescription information sent to a pharmacy or health care facility. Accordingly, one or more monitoring servers 840 may facilitate enforcement of a prescribed regimen, targeted to the characteristics of a particular smoker that is focused on the goal of assisting a smoker to break, and therefore give up, the habit of smoking. However, such examples should not be construed as limiting the scope of the monitoring that may take place in accordance with the principles of the disclosure. Any monitoring technique known in the art may be applied by server 840 based upon, e.g., the smoker statistics stored in one or more databases 850, in order to assist in the enforcement of a defined schedule.

At step 905, a doctor may utilize a workstation such as, e.g., a desktop computer, laptop computer, tablet, or a mobile phone to log into and access the cloud database in order to retrieve one or more data records received and stored in the cloud. The doctor may, e.g., submit a query to a cloud database 850 in order to retrieve data records associated with a particular smoker. The query may include, e.g., the unique smoker ID associated with a particular smoker. In response to the query submitted by the doctor, the cloud storage system may provide the data record, which includes smoker statistics, to the doctor. For purposes of the instant disclosure, a doctor may be any human user including, a physician, clinician, insurance company, insurance company agent, a friend, a family member, or any other human person.

Smoker data or statistics may include, among other things, SCig log data relating to the characteristics and conditions of the SCig 200/300, including its components (e.g., cartomizer, heater/atomizer, juice, battery, etc.), and user activity log data relating to the use of the SCig 200/300 by a user. The SCig log data may comprise data such as, e.g., date of manufacture of the SCig (and/or a component in the SCig), expiration date of the SCig (and/or a component in the SCig), amount of time the SCig has been in use (e.g., hours of operation), power supply voltage, battery type, battery remaining, number of times battery has been recharged, temperature of heater, heater type, nicotine level delivered, flavor in use, ingredient list, amount of cartomizer left, lot number, cartomizer type, cartomizer identification number, time/date of retrofitting the eCig 10 with the logging device, and the like.

The user activity log data may comprise data such as, e.g., time of each use by the user (e.g., puff time), date of each use by the user (e.g., puff date), duration of each use (e.g., puff duration), geographic location at each use (e.g., puff location), volume inhaled during each puff, puff flow rate, pressure during each use (e.g., puff draw strength or pressure), nicotine level delivered (payload) to user at each use (e.g., nicotine per puff), identification of ingredients in aerosol delivered to user at each use (e.g., ingredient identification), amount of each ingredient in aerosol deliver to user at each use (e.g., ingredient amount), user identification, user age, number of years user has been smoking, average number of cigarettes smoked per day by user, and the like. At least a subset of the smoker statistics described above may also be collected, stored, transmitted, and/or transferred via a data logging device 100 coupled to a conventional tobacco cigarette.

Figure 10A:
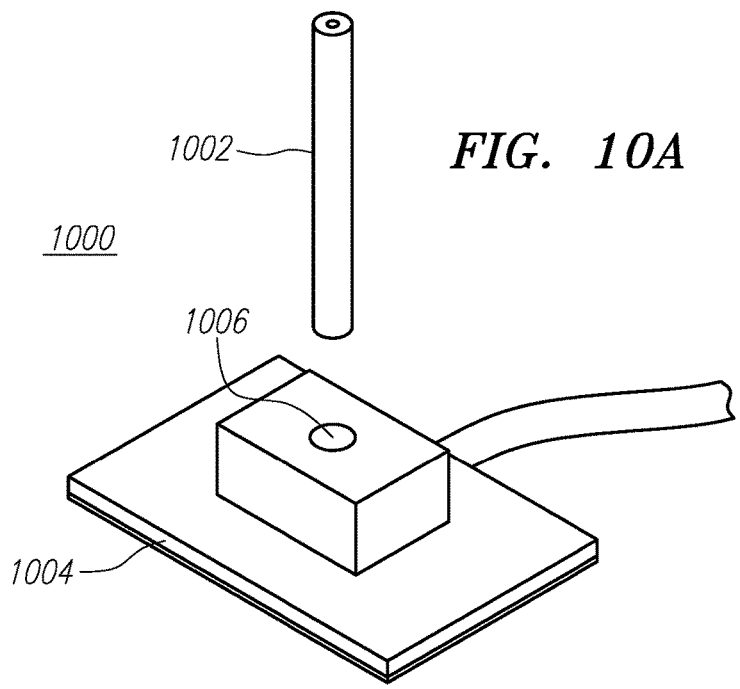
FIG. 10A shows an example of system including a docking station that may be used to directly connect an SCig to a doctor's workstation, according to one aspect of the disclosure.
Figure 16:
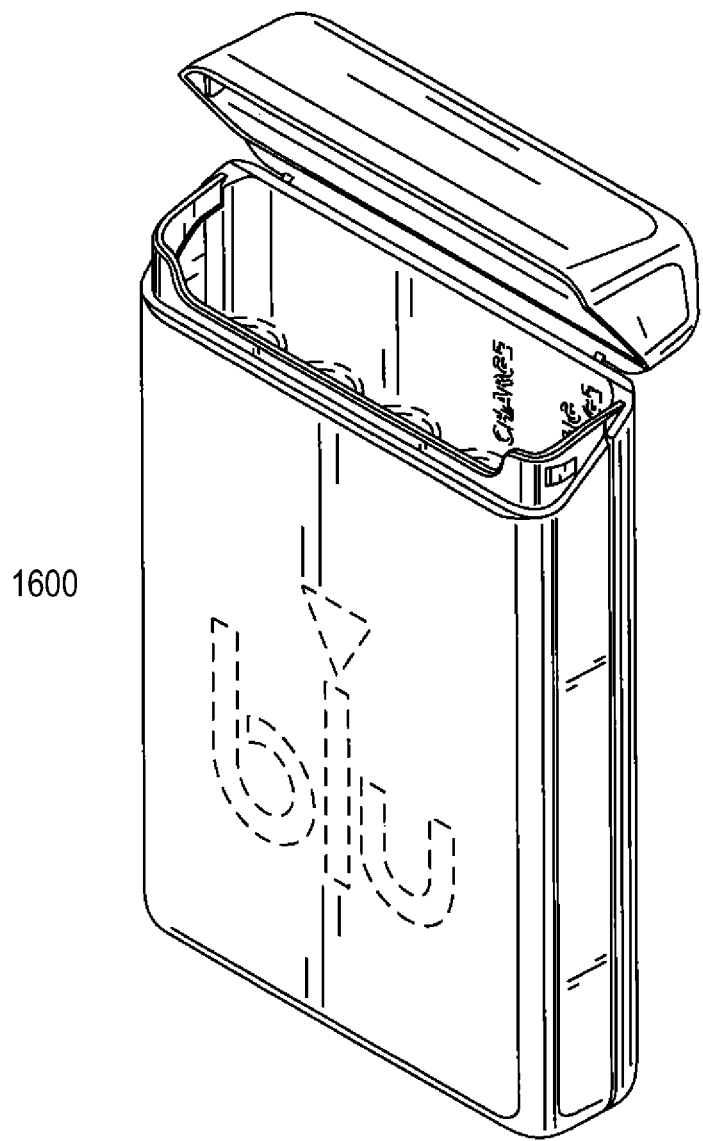
FIG. 16 is an electronic cigarette pack for receiving, storing, charging, and/or data transfer from one or more electronic cigarettes.

FIG. 10A is a schematic illustration of an example of a system 1000 including a docking station 1004 that may be used to directly connect an SCig 1002 to a doctor's workstation, according to one aspect of the disclosure. In an embodiment, the system 1000 can be a pack for receiving, storing, charging, and/or data transfer from one or more electronic cigarettes, such as the pack 1600 shown in FIG. 16 and described in United States Design Patent No. D700,994, issued on 11 Mar. 2014, which is hereby incorporated by reference as though fully set forth herein. The SCig 1002 may include an SCig 200, 401 that was manufactured to include a data logging device 100, an SCig 300, 400 created from a conventional eCig 10, 410, 510 that was retrofitted to include a data logging device 100, or a housing 610 that is attachable to a conventional tobacco cigarette and that includes a data logging device 100. The data logging device 100 can be connected to the SCig 1002, a power supply or a cartomizer (not shown) of SCig 1002, or housing 411, 610 (e.g., attached to SCig 1002 or to a conventional tobacco cigarette) via a mounting mechanism, such as spring-loaded, pressing arms 520, 540; a friction-fit suspension plate 430, 431; a ribbon cable 520, 540, 1060; a wire cluster/set 1060; a wiring harness 1060; or a socket (not shown).

A doctor may prepare the SCig 1002 for coupling with the docking station 1004 by removing a cover on one end of the SCig 1002. The doctor may then couple the SCig 1002 to a portion of the docking station 1004 configured to mate with the SCig 1002 such as, e.g., docking port 1006. In order to facilitate a direct connection to the doctor's workstation, a cable, limb, or other extremity, of the docking station may be coupled to the doctor's workstation.

Figure 10C:
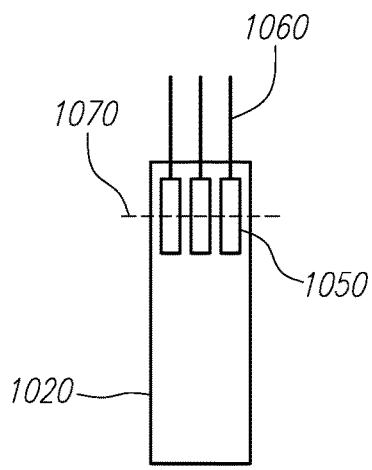
FIG. 10C is an isometric view of an embodiment of a data logging device.
Figure 10B:
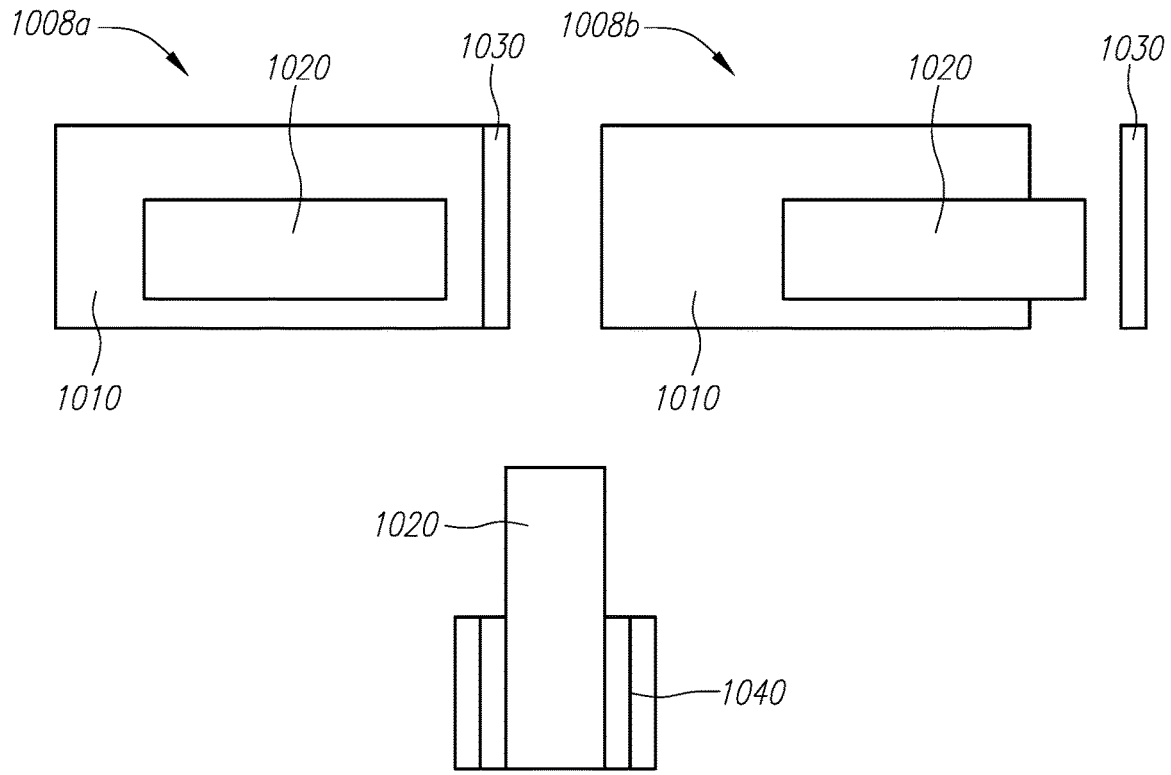
FIG. 10B shows an alternative example of a system including a docking station that may be used to directly connect a logging unit of an SCig to transfer smoker statistics to a doctor's workstation.

FIG. 10B is a schematic illustration of an alternative example of a docking station 1040 that may be used to directly connect a data logging device 1020 of an SCig in order to transfer smoker statistics to a doctor's workstation, according to one aspect of the disclosure. The data logging device 1020 may be substantially similar to the data logging device 100 described above.

State 1008a shows a fully assembled SCig that may include, among other things, e.g., an outer shell 1010, a data logging device 1020, and a cap 1030. State 1008b shows an example of an SCig after, e.g., a pair of scissors has been used to cut off the cap 1030. After the cap 1030 has been removed, then the data logging device 1020 may be removed from the outer shell 1010 of the SCig. After the data logging device 1020 has been removed from the SCig, the data logging device 1020 may be coupled to a portion of the docking station 1040 configured to mate with data logging device 1020 such as, e.g., a docking port. In order to facilitate a direct connection to the doctor's workstation, a cable, limb, or other extremity, of the docking station 1040 may be coupled to the doctor's work station.

FIG. 10C is an isometric view of an embodiment of data logging device 1020 and connecting wires 1060 that are configured to electronically communicate with an SCig. The connecting wires 1060 can be one or more single wires or a ribbon cable, for example. Also shown in FIG. 10C are edge connectors 1050, as commonly described in the computer industry. The edge connectors 1050 can be electronically connected to a power supply or cartomizer of an SCig, for example, via connecting wires 1060. The connecting wires 1060 can be directly soldered to an outer edge of the edge connectors 1050. Dashed line 1070 indicates a line along which a scissors can be used to cut the data logging device (including edge connectors 1050). Once the distal portion of the data logging device 1020 has been cut off, it can be placed in a docking station or other reader for data transfer.

Figure 11:
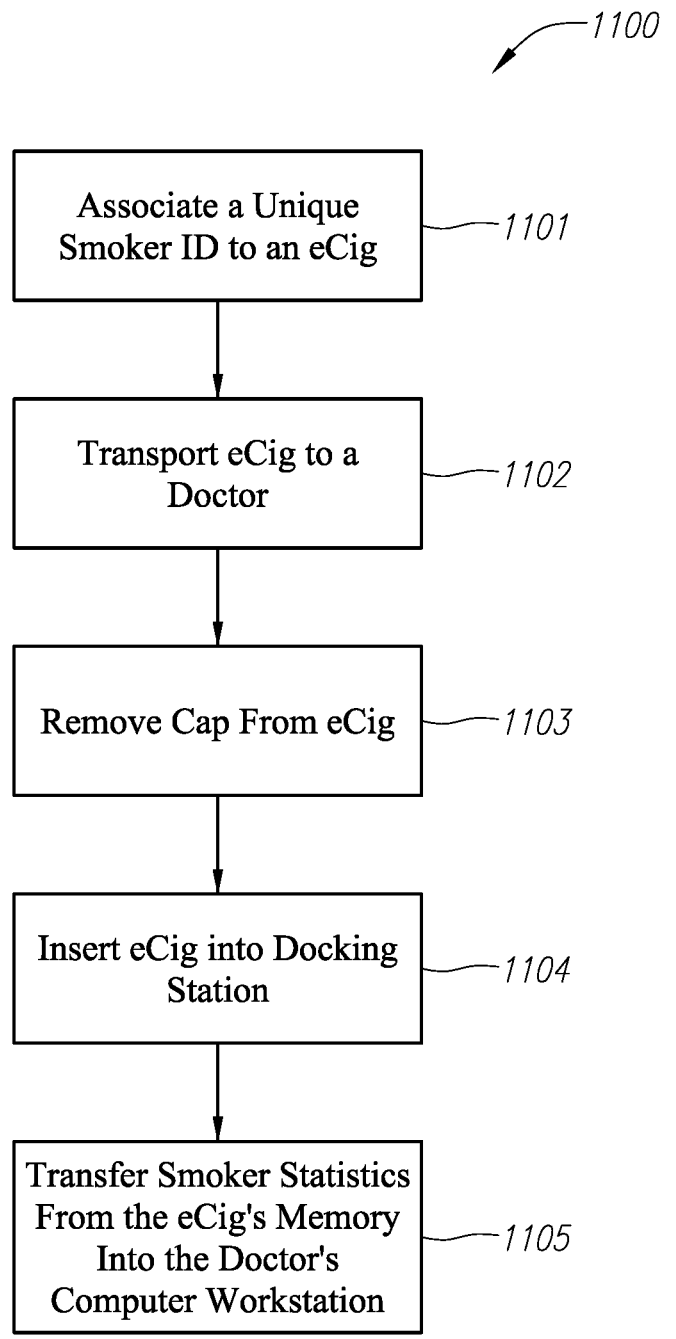
FIG. 11 shows an example of a method for collecting and transferring smoker statistics from the memory of an SCig to a doctor's workstation, according to one aspect of the disclosure.

FIG. 11 shows an example of a method for collecting and transferring smoker statistics from the memory unit 120 of an SCig to a doctor's workstation, according to one aspect of the disclosure. At step 1101, a unique smoker ID may be generated. The unique smoker ID may include any data sufficient to associate a particular smoker with a particular SCig such as, e.g., an SCig serial number, an SCig barcode, an SCig radio frequency identification device (RFID), a custom data string provided by the manufacturer of the SCig, a smoker's name, a smoker's social security number, a custom data string provided by the smoker, or the like. The unique smoker ID may be generated, e.g., at the time a user purchases the SCig, or alternatively, e.g., at a point in time later than the time a user purchases the SCig via mail, telephone, or an online transaction via a network such as, e.g., the Internet.

Step 1101 occurs after a smoker comes into possession of the SCig, becomes associated with a unique smoker ID, and begins using the SCig. While a smoker is using the SCig, microcontroller 110 (shown in FIG. 1) may interface with one or more sensors to collect smoker statistics. After collecting the smoker statistics, the microcontroller 110 may associate the unique smoker ID with the smoker statistics, e.g., in the form of a data record. The data record may then be stored in the memory unit 120 permanently or temporarily until, e.g., a data transmission or data transfer is initiated.

At step 1102, the smoker then transports the SCig to a doctor. The smoker may transport the SCig by taking the SCig to the doctor's physical location such as, e.g., a clinic or the doctor's office or residence. Alternatively, e.g., the smoker may mail the SCig, or a portion of the SCig such as, e.g., the data logging device 100, to the doctor's physical location by utilizing, e.g., the U.S. Postal Service, FedEx, UPS, or the like. After the doctor receives the SCig, or portion of the SCig, the doctor may remove the cap on one end of the SCig at step 1103 and then couple the SCig or data logging device to docking station 1004, 1040 at step 1104. At step 1105, the doctor may command the data transfer module 140 to initiate transfer of smoker statistics across a communication link. Alternatively, the data transfer module 140 may automatically initiate transfer of the smoker statistics when a connection to an external storage device is detected.

Figure 12:
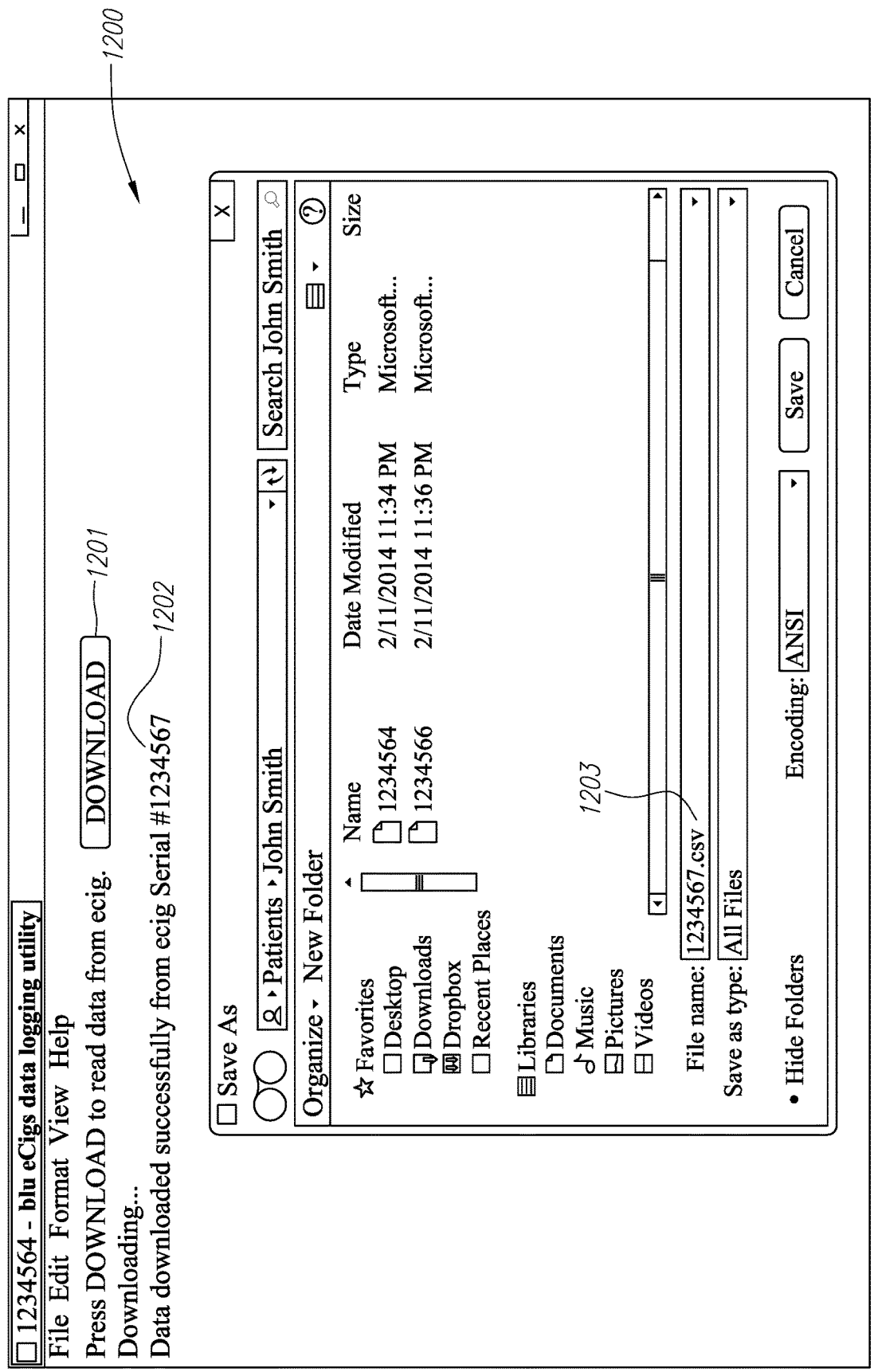
FIG. 12 shows an example of a graphical user interface that may be provided in order to facilitate data transfer of smoker statistics from the memory unit of an SCig to a doctor's workstation, according to one aspect of the disclosure.

FIG. 12 shows an example of a graphical user interface 1200 that may facilitate data transfer of smoker statistics from the memory unit 120 (shown in FIG. 1) of an SCig to a doctor's workstation, according to one aspect of the disclosure. The interface 1200 may include a transfer initiation icon 1201, a status indicator 1202, and permit the doctor to assign a name 1203 to the transferred data record comprising smoker statistics. In the example provided in FIG. 12, for instance, a doctor may command the data transfer module to initiate transfer of stored smoker statistics by, e.g., selecting the transfer initiation icon 1201. The transferred data record may be stored as, e.g., a document, spreadsheet, database, database record, or other form of file or record known in the art. In addition, the data record may be associated with the smoker ID at this step if not done previously by Scig.

Figure 13:
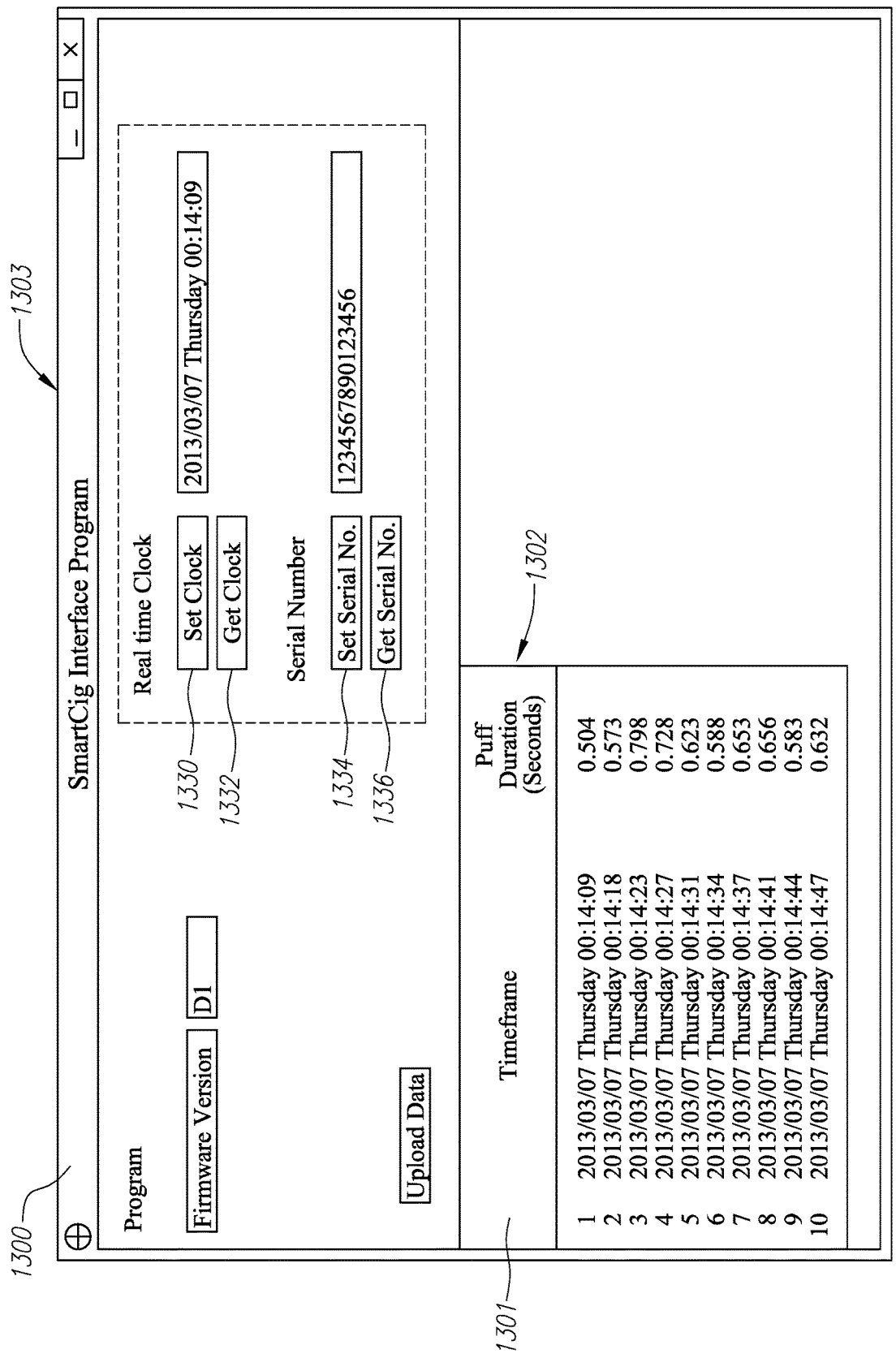
FIG. 13 shows an example of a graphical user interface that shows a report providing a subset of smoker statistics, according to one aspect of the disclosure.

FIG. 13 shows an example of a graphical user interface 1300 that shows a report providing a subset of smoker statistics, according to one aspect of the disclosure. For example, the interface 1300 may provide a report that displays a subset of smoker statistics such as, e.g., a time-stamp 1301 of each puff a smoker took while using the SCig as well as the duration of each puff 1302. A doctor may then use smoker statistics provided in the report to develop a regimen for a smoker to successfully stop smoking. For example, the doctor may review the smoker's puffs and puff durations and determine, e.g., that a smoker smoked 6 days a week for an average of 4 hours per day. The doctor may define, e.g., a first regimen schedule requiring that the smoker cut back to 6 days a week at 2 hours per day. At the end of the first regimen schedule, the doctor may analyze the smoker's smoker statistics and suggest that the smoker further cut back to 4 days a week at 2 hours per day, and the like. The doctor may make this suggestion based in part, e.g., on time stamp data collected by the SCig and retrieved by the doctor. Such an incremental regimen schedule based upon a user's actual smoker statistics may allow a doctor to reliably customize a regimen schedule that can be used to effectively wean a smoker off of cigarettes. However, such a regimen should not be viewed as limiting and it is conceivable that a doctor may utilize smoker statistics in a variety of different ways to customize a particular regimen that is targeted for a particular smoker's needs.

User interface 1300 may also include an interface portion 1303 when, e.g., the interface is being provided to an agent of the manufacturer of the SCig or another human user with sufficient permission to adjust settings of the SCig. Interface portion 1303 may be used, e.g., to facilitate setting of the SCig's real time clock 1330, 1332 associated with the data logging device 100 and setting the serial number 1334, 1336 of the SCig.

Figure 14:
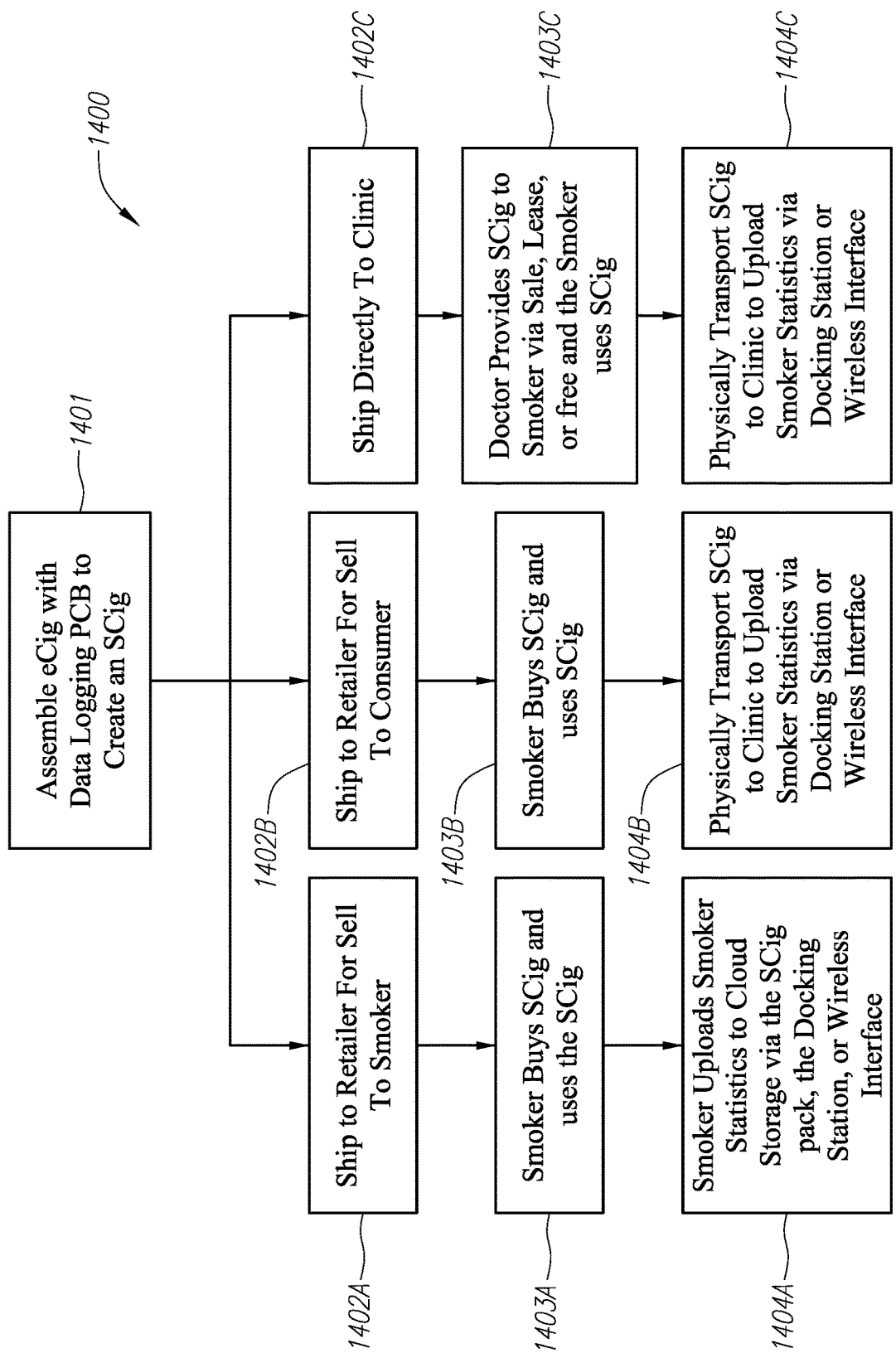
FIG. 14 shows a plurality of methods for distributing the SCig to a smoker, according to one or more aspects of the disclosure.

FIG. 14 shows a variety of methods 1400 for distributing the SCig to a smoker, according to one or more aspects of the disclosure. The methods may include one or more steps 1401 through 1404C. The smoker, or other human user, may upload or transfer smoker statistics by, e.g., using a special SCig pack or docking station.

Figure 15:
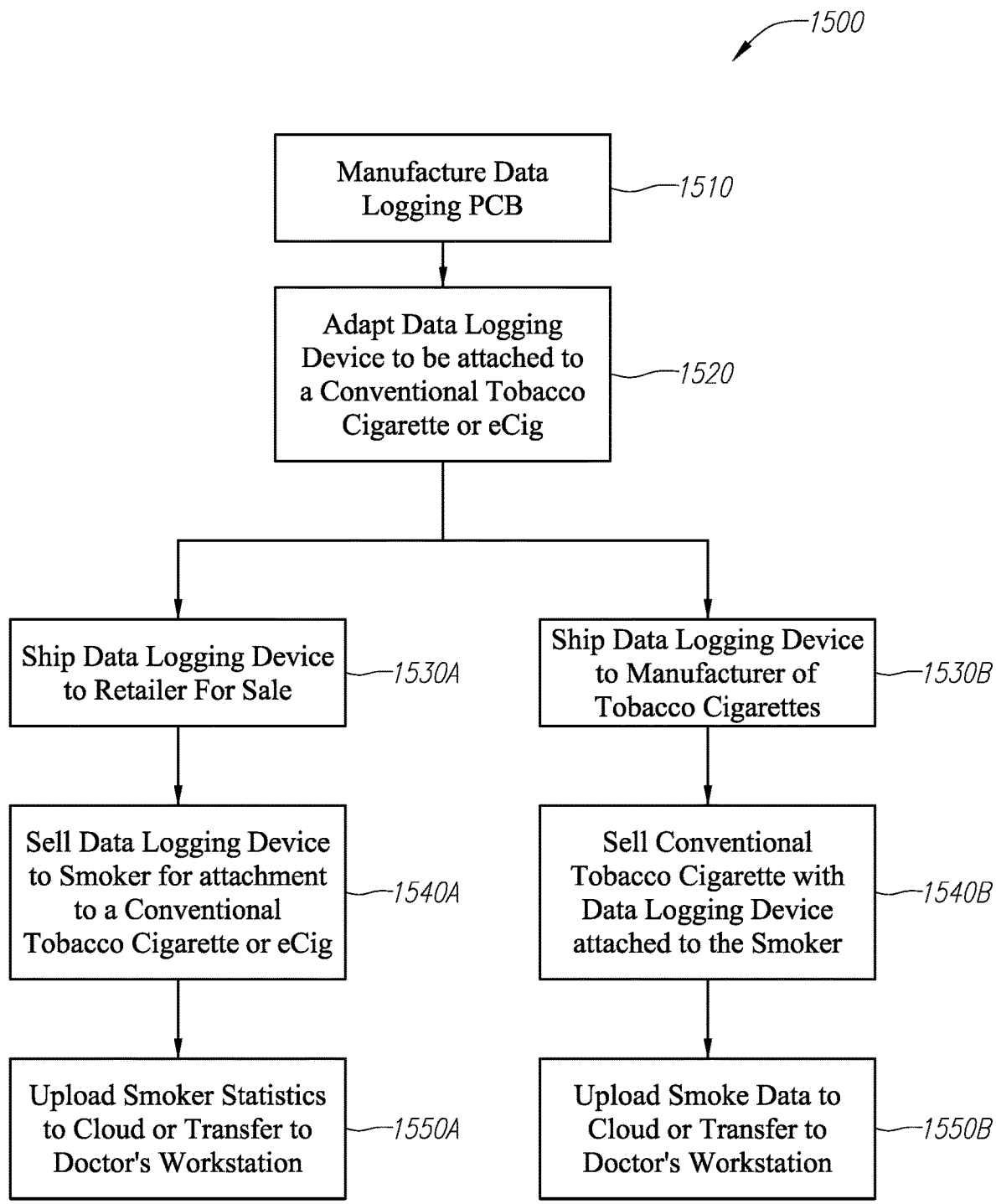
FIG. 15 shows alternative methods for distributing the disclosed data logging device, according one or more aspects of the disclosure.

FIG. 15 shows alternative methods 1500 for distributing the disclosed data logging device for use in conjunction with conventional tobacco cigarettes, according one or more aspects of the disclosure. The methods 1500 may include one or more steps 1510 through 1550A or 1550B.

According to a further aspect of the disclosure, a computer program is provided on a computer-readable medium that, when executed on a computer (e.g., microcontroller 110 and/or server 840) may cause each of the processes described herein to be carried out. The computer-readable medium may include a code section or code segment for each step of the processes described herein.

A "computer," as used in this disclosure, means any machine, device, circuit, component, or module, or any system of machines, devices, circuits, components, modules, or the like, which are capable of manipulating data according to one or more instructions, such as, for example, without limitation, a processor, a microprocessor, a central processing unit, a general purpose computer, a super computer, a personal computer, a laptop computer, a palmtop computer, a notebook computer, a desktop computer, a workstation computer, a server, or the like, or an array of processors, microprocessors, central processing units, general purpose computers, super computers, personal computers, laptop computers, palmtop computers, notebook computers, desktop computers, workstation computers, servers, or the like.

A "server," as used in this disclosure, means any combination of software and/or hardware, including at least one application and/or at least one computer to perform services for connected clients as part of a client-server architecture. The at least one server application may include, but is not limited to, for example, an application program that can accept connections to service requests from clients by sending back responses to the clients. The server may be configured to run the at least one application, often under heavy workloads, unattended, for extended periods of time with minimal human direction. The server may include a plurality of computers configured, with the at least one application being divided among the computers depending upon the workload. For example, under light loading, the at least one application can run on a single computer. However, under heavy loading, multiple computers may be required to run the at least one application. The server, or any if its computers, may also be used as a workstation.

A "database," as used in this disclosure, means any combination of software and/or hardware, including at least one application and/or at least one computer. The database may include a structured collection of records or data organized according to a database model, such as, for example, but not limited to at least one of a relational model, a hierarchical model, a network model or the like. The database may include a database management system application (DBMS) as is known in the art. The at least one application may include, but is not limited to, for example, an application program that can accept connections to service requests from clients by sending back responses to the clients. The database may be configured to run the at least one application, often under heavy workloads, unattended, for extended periods of time with minimal human direction.

A "communication link," as used in this disclosure, means a wired and/or wireless medium that conveys data or information between at least two points. The wired or wireless medium may include, for example, a metallic conductor link, a radio frequency (RF) communication link, an Infrared (IR) communication link, an optical communication link, or the like, without limitation. The wired medium may include a power supply line. The RF communication link may include, for example, WiFi, WiMAX, IEEE 802.11, DECT, OG, 1G, 2G, 3G or 4G cellular standards, Bluetooth, and the like.

A "network," as used in this disclosure means, but is not limited to, for example, at least one of a local area network (LAN), a wide area network (WAN), a metropolitan area network (MAN), a personal area network (PAN), a campus area network, a corporate area network, a global area network (GAN), a broadband area network (BAN), a cellular network, the Internet, or the like, or any combination of the foregoing, any of which may be configured to communicate data via a wireless and/or a wired communication medium. These networks may run a variety of protocols not limited to TCP/IP, IRC or HUP.

A "computer-readable medium," as used in this disclosure, means any medium that participates in providing data (for example, instructions) which may be read by a computer. Such a medium may take many forms, including non-volatile media, volatile media, and transmission media. Non-volatile media may include, for example, optical or magnetic disks and other persistent memory. Volatile media may include dynamic random access memory (DRAM). Transmission media may include coaxial cables, copper wire and fiber optics, including the wires that comprise a system bus coupled to the processor. Transmission media may include or convey acoustic waves, light waves and electromagnetic emissions, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, a carrier wave as described hereinafter, or any other medium from which a computer can read. The computer-readable medium may include a "Cloud," which includes a distribution of files across multiple (e.g., thousands of) memory caches on multiple (e.g., thousands of) computers.

Various forms of computer readable media may be involved in carrying sequences of instructions to a computer. For example, sequences of instruction (i) may be delivered from a RAM to a processor, (ii) may be carried over a wireless transmission medium, and/or (iii:) may be formatted according to numerous formats, standards or protocols, including, for example, WiFi, WiMAX, IEEE 802.11, DECT, OG, 1G, 2G, 30 or 4G cellular standards, Bluetooth, or the like.

The terms "including," "comprising," and variations thereof, as used in this disclosure, mean "including, but not limited to," unless expressly specified otherwise.

The terms and "the," as used in this disclosure, means "one or more," unless expressly specified otherwise.

Devices that are in communication with each other need not be in continuous communication with each other, unless expressly specified otherwise. In addition, devices that are in communication with each other may communicate directly or indirectly through one or more intermediaries.

Although process steps, method steps, algorithms, or the like, may be described in a sequential order, such processes, methods and algorithms may be configured to work in alternate orders. In other words, any sequence or order of steps that may be described does not necessarily indicate a requirement that the steps be performed in that order. The steps of the processes, methods or algorithms described herein may be performed in any order practical. Further, some steps may be performed simultaneously.

When a single device or article is described herein, it will be readily apparent that more than one device or article may be used in place of a single device or article. Similarly, where more than one device or article is described herein, it will be readily apparent that a single device or article may be used in place of the more than one device or article. The functionality or the features of a device may be alternatively embodied by one or more other devices which are not explicitly described as having such functionality or features.

While the disclosure has been described in terms of exemplary embodiments, those skilled in the art will recognize that the disclosure can be practiced with modifications that fall within the spirit and scope of the appended claims. These examples given above are merely illustrative and are not meant to be an exhaustive list of all possible designs, embodiments, applications or modification of the disclosure.

Although embodiments of a data logging device for use with a clinical interface have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the devices. Joinder references (e.g., affixed, attached, coupled, connected, and the like) are to be construed broadly and can include intermediate members between a connection of elements and relative movement between elements. As such, joinder references do not necessarily infer that two elements are directly connected and in fixed relationship to each other. It is intended that all matter contained in the above description or shown in the accompanying drawings shall be interpreted as illustrative only and not limiting. Changes in detail or structure can be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Various embodiments have been described above to various apparatuses, systems, and/or methods. Numerous specific details have been set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated above are non-limiting examples, and thus it can be appreciated that the specific structural and functional details disclosed above may be representative and do not necessarily limit the scope of the embodiments, the scope of which is defined solely by the appended claims.

Reference throughout the specification to "various embodiments," "some embodiments," "one embodiment," or "an embodiment," or the like, means that a particular feature, structure, or characteristic described in connection with the embodiment is included in at least one embodiment. Thus, appearances of the phrases "in various embodiments," "in some embodiments," "in one embodiment," or "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

What is claimed:

1. A system for collecting and transmitting smoker data for an electronic cigarette, the system comprising the following:
    an electronic cigarette power supply comprising the following:
        a tubular housing; and
        a battery mounted within the tubular housing; and
    a data logging device irremovably coupled to and within the tubular housing, wherein the data logging device is suspended within the tubular housing by spring-loaded, pressing arms, and further wherein the data logging device is configured to collect and wirelessly transmit smoker data collected during use of the electronic cigarette.

2. The system of claim 1, wherein the mounting mechanism is selected from the group consisting of spring-loaded, pressing arms; a friction-fit suspension plate; a ribbon cable; a wire cluster/set; a wiring harness; and a socket.

3. The system of claim 1, wherein the data logging device further comprises an edge connector.

4. The system of claim 3, further comprising a ribbon cable electrically connecting the battery to the edge connector.

5. The system of claim 3, further comprising at least one electrical wire connecting the battery to the edge connector, whereby the data logging device is separable from the at least one electrical wire by severing the edge connector inboard from a location where the at least one electrical wire is connected to the edge connector.

6. The system of claim 5, wherein the at least one electrical wire is directly soldered to an outer edge of the edge connector.

7. A system for collecting and transmitting smoker data for an electronic cigarette, the system comprising the following:
- an electronic cigarette cartomizer comprising the following:
  - a tubular housing; and
  - a heater mounted within the tubular housing; and
- a data logging device irremovably coupled to and within the tubular housing, wherein the data logging device comprises spring-loaded, pressing arms that suspend the data logging device within the tubular housing, and further wherein the data logging device is configured to collect and wirelessly transmit smoker data collected during use of the electronic cigarette.

8. The system of claim 7, wherein the mounting mechanism is selected from the group consisting of spring-loaded, pressing arms; a friction-fit suspension plate; a ribbon cable; a wire cluster/set; a wiring harness; and a socket.

9. The system of claim 7, wherein the data logging device further comprises an edge connector.

10. The system of claim 9, further comprising a ribbon cable electrically connecting the heater to the edge connector.

11. The system of claim 9, further comprising at least one electrical wire connecting the heater to the edge connector, whereby the data logging device is separable from the at least one electrical wire by severing the edge connector inboard from a location where the at least one electrical wire is connected to the edge connector.

12. The system of claim 11, wherein the at least one electrical wire is directly soldered to an outer edge of the edge connector.

13. A system for collecting and transmitting smoker data for an electronic cigarette, the system comprising the following:
- an electronic cigarette power supply comprising the following:
  - a tubular housing; and
  - a battery mounted within the tubular housing; and
- a data logging device irremovably coupled to and within the tubular housing, wherein the data logging device comprises a mounting mechanism configured to suspend the data logging device within the tubular housing, and further wherein the data logging device is configured to collect and transmit smoker data collected during use of the electronic cigarette, wherein the data logging device further comprises an edge connector; and
- at least one electrical wire connecting the battery to the edge connector, whereby the data logging device is separable from the at least one electrical wire by severing the edge connector inboard from a location where the at least one electrical wire is connected to the edge connector.

14. The system of claim 13, wherein the at least one electrical wire is directly soldered to an outer edge of the edge connector.

15. A system for collecting and transmitting smoker data for an electronic cigarette, the system comprising the following:
- an electronic cigarette cartomizer comprising the following:
  - a tubular housing; and
  - a heater mounted within the tubular housing; and
- a data logging device irremovably coupled to and within the tubular housing, wherein the data logging device comprises a mounting mechanism configured to suspend the data logging device within the tubular housing, and further wherein the data logging device is configured to collect and transmit smoker data collected during use of the electronic cigarette, wherein the data logging device further comprises an edge connector; and
- at least one electrical wire connecting the heater to the edge connector, whereby the data logging device is separable from the at least one electrical wire by severing the edge connector inboard from a location where the at least one electrical wire is connected to the edge connector.

16. The system of claim 15, wherein the at least one electrical wire is directly soldered to an outer edge of the edge connector.

* * * * *